(12) United States Patent
Konishi et al.

(10) Patent No.: US 9,149,434 B2
(45) Date of Patent: Oct. 6, 2015

(54) CORE PARTICLE FOR PHARMACEUTICAL PREPARATION

(75) Inventors: Masashi Konishi, Naruto (JP); Shouichi Oonishi, Naruto (JP); Akira Ookubo, Naruto (JP); Masashi Yunoki, Naruto (JP); Ariumi Kawamoto, Naruto (JP); Kanako Hattori, Naruto (JP)

(73) Assignee: TOMITA PHARMACEUTICAL CO., LTD., Naruto-shi, Tokushima (JP)

( * ) Notice: Subject to any disclaimer, the term of this patent is extended or adjusted under 35 U.S.C. 154(b) by 0 days.

(21) Appl. No.: 12/745,851

(22) PCT Filed: Sep. 8, 2008

(86) PCT No.: PCT/JP2008/066159
§ 371 (c)(1),
(2), (4) Date: Jun. 2, 2010

(87) PCT Pub. No.: WO2009/072334
PCT Pub. Date: Jun. 11, 2009

(65) Prior Publication Data
US 2010/0260856 A1    Oct. 14, 2010

(30) Foreign Application Priority Data
Dec. 3, 2007    (JP) .................... 2007-312894

(51) Int. Cl.
*A61K 9/16*    (2006.01)
*A61K 47/02*    (2006.01)

(52) U.S. Cl.
CPC ............. *A61K 9/1611* (2013.01); *A61K 9/1676* (2013.01); *A61K 47/02* (2013.01)

(58) Field of Classification Search
CPC ...... A61K 36/82; A61K 36/185; A61K 36/22
See application file for complete search history.

(56) References Cited

U.S. PATENT DOCUMENTS

| 4,632,843 A | * | 12/1986 | Pich et al. .................. 423/499.1 |
| 4,983,593 A | | 1/1991 | Miyajima et al. |

FOREIGN PATENT DOCUMENTS

| JP | 2-49728 | 2/1990 |
| JP | 2-258719 | 10/1990 |
| JP | 5-49901 | 3/1993 |
| JP | 6-205959 | 7/1994 |
| JP | 7-173050 | 7/1995 |

(Continued)

OTHER PUBLICATIONS

Joguet et al, Preparation of Nanosized Drug Particles by the Coating of Inorganic Cores: Naproxen and Ketoprofen on Alumina, 2002, Journal for Colloid and Interface Science, 251, pp. 284-287.*

*Primary Examiner* — Trevor Love
(74) *Attorney, Agent, or Firm* — Fox Rothschild LLP (57) ABSTRACT

The present invention provides a core particle for a pharmaceutical preparation which features the requisite properties of a core particle, and which has enough chemical stability, and in which reactivity with the drug (an active pharmaceutical ingredient) is limited or prevented. More specifically, the present invention relates to a core particle wherein a film containing an active pharmaceutical ingredient can be formed on the surface thereof, and (1) the core particle comprises a pharmaceutically acceptable inorganic material, (2) the inorganic material is poorly soluble in water, and (3) pH of a solution of the inorganic material is 5 to 8.

12 Claims, 1 Drawing Sheet

(56) References Cited

FOREIGN PATENT DOCUMENTS

| JP | 9-175999 | 7/1997 |
| JP | 3219787 | 10/2001 |
| JP | 2003-137771 | 5/2003 |
| JP | 3447042 | 9/2003 |
| WO | 2006/023286 | 3/2006 |

* cited by examiner

CORE PARTICLE FOR PHARMACEUTICAL PREPARATION

TECHNICAL FIELD

The present invention relates to a core particle for pharmaceutical preparation for forming a film containing an active ingredient (active pharmaceutical ingredient) on the surface thereof.

BACKGROUND ART

One technique for manufacturing pharmaceutical products employs a means wherein core particles are prepared in a fluidized state, a drug (active ingredient) either alone or mixed with an excipient is introduced thereinto, and the drug or mixture coats the surface of the core particles. In such a case, the requirements for the core particles are: 1) they are generally spherical and of a uniform size, and 2) the core particles do not break up during the coating step (i.e., they have a specified mechanical strength).

Organic materials have mainly been used for prior art core particles. For example, there are core particles of crystalline cellulose alone (Patent Document 1), core particles of a sugar alone (Patent Document 2), core particles comprising a sugar and crystalline cellulose (Patent Document 3), core particles comprising a sugar and a starch (Patent Document 4), and core particles using a single substance selected from a group of consisting of a sugar alcohol, vitamin C, and sodium chloride (Patent Document 5).

To stabilize a drug that is unstable in an acid, however, the surfaces of the core particles disclosed in Patent Documents 1 to 4 must be coated with a layer comprising a basic substance (e.g., magnesium carbonate) and an organic binder before being coated with the drug.

In addition, with the core particles of crystalline cellulose alone disclosed in Patent Document 1, if the surfaces of the core particles are not properly coated with the drug, the drug does not completely dissolve in the body because disintegration in the gastrointestinal tract (particularly the stomach) after oral administration requires too much time, and the desired absorption via the gastrointestinal tract cannot be achieved.

Sugar or sodium chloride is used in the core particles of Patent Documents 2 to 5, and therefore the sugar or sodium chloride gets dissolved away by the infiltration of water, shape retention of the particles becomes poor during processing, and therefore sustained release cannot be stably maintained. In addition, if a water-based solvent is used during the coating process, the particles are more likely to cohere to each other and adhere to the container wall of the granulator. Additionally, when such a preparation is administered to diabetic patients, the sugar or salt burden becomes a problem in treating the diabetes.

Furthermore, the core particles of sugar alone disclosed in Patent Document 2 lack hardness, so the particles break up in the coating step and become a powder.

Not only do the core particles comprising sugar and starch disclosed in Patent Document 4 have insufficient hardness, but because sucrose, which has needle-shaped crystals, is used as the sugar, the surface is very uneven resulting in a high degree of friability. Furthermore, it is known that when a reducing sugar is used as the sugar as in Patent Document 4, discoloration may occur due to a chemical reaction if an amino compound or organic acid is used as the active ingredient.

Finally, when an inorganic substance is used as the structural material of core particles such as in Patent Documents 1 to 5, there is a limit to the processing temperature, and processing (drying) requires a long time.

Patent Document 1: Japanese Patent Application Publication No. H7-173050
Patent Document 2: Japanese Patent Application Publication No. H6-205959
Patent Document 3: Japanese Patent No. 3219787
Patent Document 4: Japanese Patent Application Publication No. H9-175999
Patent Document 5: Japanese Patent No. 3447042

DISCLOSURE OF THE INVENTION

Therefore, a main object of the present invention is to provide a core particle for pharmaceutical preparation featuring the requisite properties of a core particle and having enough chemical stability that reactivity with the drug (active ingredient) is reduced or prevented.

After careful consideration of the problems inherent in the prior art, the inventors conducted intensive research and discovered that the above object can be attained by using a specific inorganic material as a core particle, thus completing the present invention.

More specifically, the present invention relates to a core particle for a pharmaceutical preparation described as follows:

1. A core particle for pharmaceutical preparation of a drug-containing particle comprising the core particle and a film containing a pharmaceutical ingredient formed on the surface of the core particle, wherein
   (1) the core particle comprises a pharmaceutically acceptable inorganic material,
   (2) the inorganic material is poorly soluble in water, and
   (3) the pH of the inorganic material is 5 to 8.

2. The core particle for pharmaceutical preparation according to claim 1, wherein particle hardness of the core particle is at least 200 g/mm$^2$.

3. The core particle for pharmaceutical preparation according to claim 1, having a particle size distribution of no more than 5 wt % of a particle having a diameter less than 45 μm, at least 90 wt % of a particle having a diameter at least 45 μm but less than 500 μm, and no more than 5 wt % of a particle having a diameter at least 500 μm.

4. The core particle for pharmaceutical preparation according to claim 1, having a particle size distribution of no more than 5 wt % of a particle with a diameter less than 45 μm, at least 90 wt % of a particle with a diameter at least 45 μm but less than 150 μm, and no more than 5 wt % of a particle with a diameter at least 150 μm.

5. The core particle for pharmaceutical preparation according to claim 1, wherein the core particle is formulated so that at least 90 wt % thereof is a pharmaceutically acceptable inorganic material.

6. The core particle for pharmaceutical preparation according to claim 1, wherein the inorganic material has a solubility in water of no more than 1 g/30 mL at 20° C.

7. The core particle for pharmaceutical preparation according to claim 1, wherein the inorganic material is at least one substance selected from calcium hydrogen phosphate, silicon dioxide, aluminum hydroxide, and aluminum silicate.

8. The core particle for pharmaceutical preparation according to claim 1, wherein an average particle size is at least 50 μm.

9. The core particle for pharmaceutical preparation according to claim 1, obtained by granulation of a composition containing the inorganic material.

10. The core particle for pharmaceutical preparation according to claim 1, wherein the inorganic material contains fine particles of calcium hydrogen phosphate represented by the formula $CaHPO_4 \cdot nH_2O$ wherein n represents 0 n and wherein (1) an average secondary particle size of the fine particles is no more than 15 μm, and (2) a static apparent specific volume of the fine particles is less than 5 mL/g.

11. The core particle for pharmaceutical preparation according to claim 10, wherein the pH of the fine particles lies within a range of 6 to 8.

12. The core particle for pharmaceutical preparation according to claim 10, wherein a crystallite size of the fine particles is no more than 300 Å.

13. The core particle for pharmaceutical preparation according to claim 10, wherein the static apparent specific volume of the fine particles is no more than 4.8 mL/g.

14. The core particle for pharmaceutical preparation according to claim 10, obtained by granulation of a composition containing the fine particles.

15. A drug-containing particle, obtained by forming a film containing a pharmaceutical ingredient on the surface of the core particle for pharmaceutical preparation according to claim 1.

16. The drug-containing particle according to claim 15, wherein the film contains a pharmaceutical ingredient and excipient.

17. A process for producing a drug-containing particle, the process comprising a step of forming a film containing a pharmaceutical ingredient on the surface of the core particle for pharmaceutical preparation according to claim 1.

ADVANTAGES OF THE INVENTION

The core particle for a pharmaceutical preparation of the present invention is formed from the specified inorganic material, and it has the requisite properties (monodispersity, flow properties, particle hardness, liquidity, etc.) of a core particle. Therefore, it is chemically stable, and it can effectively limit or prevent reactivity with the drug (active ingredient). As a result, it can suitably be used as a core particle wherein a film containing an active ingredient is formed on the surface thereof. In other words, the core particle of the present invention can be used in a variety of pharmaceutical products without regard to the type of active ingredient to be used. Particularly when calcium hydrogen phosphate, etc., is used as the inorganic material, effectiveness in suppressing reactivity, etc., can be obtained with even more certainty.

BEST MODE FOR CARRYING OUT THE INVENTION

The core particle for pharmaceutical preparation of the present invention is a core particle wherein a film containing an active pharmaceutical ingredient is to be formed on the surface thereof, and wherein (1) the core particle comprises a pharmaceutically acceptable inorganic material;

(2) the inorganic material is poorly soluble in water; and (3) the pH of the inorganic material is 5 to 8.

1. Core Particle for Pharmaceutical Preparation

The core particle for pharmaceutical preparation of the present invention is one wherein a film containing an active ingredient (active pharmaceutical ingredient) can be formed on the surface of the core particle. In other words, it is a core particle (hereinafter, also called the "core particle of the present invention") to be used in pharmaceuticals that have a so-called core-shell structure.

The core particle of the present invention contains a pharmaceutically (pharmacologically) acceptable inorganic material. A substance that is poorly soluble in water is used for this inorganic material. In particular, an inorganic material that has a solubility in water of no more than 1 g/30 ml, and preferably no more than 1 g/100 mL, at 20° C. can be preferably used therefor. Shape retention is lost due to infiltration by water when a water soluble material is used, but the present invention enables stable shape retention, etc., to be realized by using an inorganic material that is poorly soluble in water.

Furthermore, the inorganic material of the core particle of the present invention has a pH of 5 to 8, preferably 6 to 8, and more preferably 6.5 to 7.5. If the pH in solution falls below 5 or rises above 8, the number of active ingredients that can be used therewith is limited, which narrows the range of use.

The type of inorganic material is not particularly limited herein provided it is hardly soluble in water and it has a pH of 5 to 8; thus, publicly known and commercially available inorganic materials used for pharmaceutical preparations can be used therefor. Examples thereof include at least one type of hydrate or anhydride of a phosphate, silicate, oxide, or hydroxide that is poorly soluble in water and has a pH of 5 to 8. More specifically, at least one selected from calcium hydrogen phosphate, silicon dioxide, aluminum hydroxide and aluminum silicate can be preferably used therefor.

The recipe of the core particle of the present invention is not particularly limited herein, but preferably the inorganic material will normally constitute at least 0.80 wt %, preferably at least 90 wt %, and more preferably 95 to 100 wt % thereof. Excellent shape retention, etc., can be exhibited by establishing a recipe in the above range. If the content of the inorganic material in the core particle of the present invention is less than 100 wt %, a generally used additive to pharmaceutical products (for example, excipient, disintegrant, desiccant, stabilizer, and binder) can be included therein in addition to the inorganic material. In such a case, a mode wherein an active ingredient is not contained in the core particle of the present invention (i.e., a core particle for pharmaceutical preparation that does not contain an active ingredient) is also encompassed by the present invention.

The shape of the core particle of the present invention is not particularly limited herein, and the shape can be either spherical, cylindrical, lamellar, irregular, etc. In general, however, a spherical shape is desirable from the standpoint of flow properties, etc.

The hardness of the core particle of the present invention is not particularly limited herein, but normally a hardness of at least 200 g/mm² is desirable. By establishing the particle hardness within the above range, it is possible to effectively prevent the core particles from breaking up and turning into a powder in the coating step wherein a film containing the active ingredient is formed on the surface of the core particle of the present invention. In this case, the upper limit of hardness is not particularly limited herein, and in general about 3000 g/mm² will be satisfactory.

Generally speaking, the average particle size of the core particle of the present invention can be suitably established in a range of at least 45 μm, preferably 45 to 500 μm, and more preferably 45 to 350 μm.

A desirable particle size distribution comprises no more than 5 wt % (preferably no more than 2 wt %) with a diameter less than 45 μm, at least 90 wt % (preferably at least 96 wt %)

with a diameter at least 45 μm but less than 500 μm, and no more than 5 wt % (preferably no more than 2 wt %) with a diameter at least 500 μm.

Therefore, core particles with the kind particle size distribution exemplified by A) to C) below can be suitably employed in the present invention.

A) No more than 5 wt % (preferably no more than 2 wt %) of particles with a diameter of less than 45 μm, at least 90 wt % (preferably at least 96 wt %) with a diameter at least 45 μm but less than 350 μm, and no more than 5 wt % (preferably no more than 2 wt %) with a diameter at least 350 μm.

B) No more than 5 wt % (preferably no more than 2 wt %) of particles with a diameter of less than 45 μm, at least 90 wt % (preferably at least 96 wt %) with a diameter at least 45 μm but less than 150 μm, and no more than 5 wt % (preferably no more than 2 wt %) with a diameter at least 150 μm.

C) No more than 5 wt % (preferably no more than 2 wt %) of particles with a diameter of less than 350 μm, at least 90 wt % (preferably at least 96 wt %) with a diameter at least 350 μm but less than 500 μm, and no more than 5 wt % (preferably no more than 2 wt %) with a diameter at least 500 μm.

The core particles of A) and B) above have a relatively small diameter, and when used for a tablet, powdered medicine, etc., they can provide a drug that feels smooth to the tongue and is easy to take. Using organic core particles makes it impossible or nearly impossible to obtain such fine core particles, so a major feature of the present invention includes the underlying premise of using an inorganic material therefor. In addition, the core particles of C) above have a relatively large diameter, and they can be suitably used, for example, as core particles in a drug for filling a capsule, etc.

The bulk density of the core particles of the present invention is generally set to about 0.2 to 1.2 g/mL, preferably 0.4 to 1.0 g/mL, and this is desirable from the standpoint of ease of processing, etc.

The angle of repose of the core particle (powder) of the present invention is normally set to no more than 40°, preferably no more than 37°, and more preferably no more than 35°, and this is preferred for uniform loading and unloading of the equipment, for forming a homogenous coating layer, etc.

The core particle of the present invention is preferably obtained by granulating a composition (raw material powder) containing the above inorganic material. In addition to the inorganic material, the raw material powder can contain the additives noted above as needed. The method described in section 2 below, for example, can be suitably used as the granulation method.

The core particle of the present invention can be used by forming a film containing an active ingredient on the surface thereof. For example, a desired drug-containing particle (a pharmaceutical product) can be produced by coating a composition comprising an active ingredient onto the surface of the core particle of the present invention.

The active ingredient is not particularly limited herein, and examples include a cholesterol-lowering agent, anti-ulcer drug, hypotensive drug, antidepressant, anti-asthma drug, antiepileptic, antiallergic agent, antimicrobial drug, anticancer drug, analgesic, anti-inflammatory agent, drug for diabetes mellitus, metabolic antagonist, osteoporosis drug, antiplatelet agent, antiemetic agent, hormone agent, anesthetic, and the like.

In addition, the composition can also contain pharmaceutical additives as needed such as a excipient, disintegrant, desiccant, stabilizer, binder, etc. The content of the pharmaceutical additive can be suitably established according to the type of additive, content of the active ingredient, etc.

The method of coating the composition containing the active ingredient onto the surface of the core particles of the present invention is not particularly limited herein, and a publicly known granulation method, for example, a stirred granulation method, fluidized bed granulation method, tumbling granulation method, etc., can be used. In this case, granulation can be performed using a publicly known or commercially available granulator. In such an instance, the thickness of the film containing the active ingredient can normally be adjusted to a range of about 1 to 100 μm.

2. Method for Manufacturing Core Particle for Pharmaceutical Preparation

The core particle of the present invention can be obtained, for example, by granulation of a fine powder of inorganic material (raw material powder) to constitute the intended core particle.

For the raw material powder, a fine powder of the various inorganic materials listed above can be used provided it is a pharmaceutically permissible inorganic material, is poorly soluble in water, and has a pH of 5 to 8.

The average particle diameter of the raw material powder can be suitably determined according to the desired particle size, etc., of the core particle of the present invention, and normally it will be 0.1 to 40 μm, preferably 0.1 to 20 μm.

When calcium hydrogen phosphate is used as the inorganic material in the present invention, it is desirable to use fine particles of calcium hydrogen phosphate which is represented by the formula $CaHPO_4 \cdot nH_2O$ (wherein n represents $0 \leq n \leq 50.5$), and in which (1) the average secondary particle diameter of the fine particles is no more than 15 μm, and (2) the static apparent specific volume is less than 5 mL/g, as the raw material powder. An embodiment using this calcium hydrogen phosphate is described in detail in the <Embodiment> section below.

The granulation method is not particularly limited herein, and any of the following, for example, can be used: tumbling granulation methods, stirred granulation methods, fluidized bed granulation methods, compression molding methods, film formation treatment methods, magnetic property treatment methods, surface modification methods, sintered molding methods, vibration molding methods, pressure swing methods, and vacuum molding methods, etc. The granulation may be performed using a conventional or commercially available granulation device. Among these granulation methods, granulation can be more suitably performed in the present invention by a stirred granulation method.

Either wet granulation or dry granulation can be used, but granulation in the present invention can be more suitably performed by wet granulation. The type of medium is not particularly limited herein, and water or a water-based medium can be suitably used. As a water-based medium, for example, an ethanol/water mixed medium (ethanol:water=approximately 1:1-5 v/v) can be suitably used. The amount of medium used can be normally range from 30 to 300 parts by weight in relation to 100 parts by weight of raw material powder.

As one example of a preferred method, granulation can be performed using a high-speed mixer/granulator (batch granulator) by loading the raw material powder into the granulator and stirring with the stirrer while spraying the medium thereinto to make a fluidized mixture. When an agitator and chopper are used as the stirrer in the above batch granulator, granulation can be more suitably performed, for example, by setting the agitator speed to about 500 to 1000 rpm and the chopper speed to about 1000 to 1500 rpm. The wet granulation product that is formed can be dried inside the granulator (hopper) or the wet granulation product can be removed from the granulator (hopper) and dried. The core particles of the present invention can subsequently be obtained by sorting the dried granulation product to achieve the desired particle size distribution.

EMBODIMENT

One example of an embodiment using calcium hydrogen phosphate (noted above) as the raw material powder is presented below.

The calcium hydrogen phosphate is basically anhydrous calcium hydrogen phosphate, and preferably n in the above formula represents $0 \leq n \leq 0.2$.

A monoclinic system is one example of the crystal system of the calcium hydrogen phosphate, but the crystal system of the calcium hydrogen phosphate is not particularly limited herein.

The average secondary particle size of the calcium hydrogen phosphate fine particles normally is no more than 15 μm, preferably no more than 10 μm, and more preferably no more than 8.5 μm. For example, fine particles with an average secondary particle size of 1 to 10 μm can be suitably used. When the average secondary particle size exceeds 15 μm, the forming properties (binding properties) decrease. The lower limit of the average secondary particle size is not particularly limited herein, but normally it is about 0.5 μm.

The static apparent specific volume of the calcium hydrogen phosphate fine particles is normally less than 5 mL/g, preferably no more than 4.8 mL/g, more preferably no more than 4.5 mL/g, and most preferably no more than 4 mL/g. The lower limit of the static apparent specific volume is not particularly limited herein, but normally it is about 2 mL/g. Therefore, for example, normally fine particles having a static apparent specific volume of 2 to 4 mL/g can be suitably used. When the static apparent specific volume exceeds 5 mL/g, not only do the handling properties decrease, but the mixing properties when the fine particles are mixed with other components also decrease. In prior art it has been considered necessary to establish a static apparent specific volume of at least 5 mL/g to maintain good forming properties, etc., but the present invention defies such common technical knowledge by developing technology wherein the static apparent specific volume is established at less than 5 mL/g, thereby improving handling and mixing properties while maintaining good forming properties.

The calcium hydrogen phosphate normally has a liquidity pH of 6 to 8, preferably 6.5 to 8, more preferably 6.5 to 7.5, and most preferably 6.7 to 7.3. When the pH in solution is set to a range of 6 to 8, the type of drug (substance) to be mixed with the core particles of the present invention is not restricted (regardless of the pH of the co-present drug (substance)), and this essentially enables stable mixing with all kinds of components.

The crystallite size or grain size of the calcium hydrogen phosphate is not particularly limited herein, but generally is no more than 300 Å, preferably no more than 250 Å, and more preferably no more than 220 Å. The lower limit of the crystallite size is not particularly limited herein, but normally will be about 100 Å. Therefore, for example, a crystallite size of 100 to 220 Å can be suitably used. Setting the range of the crystallite size at no more than 300 Å enables even better coherence, and therefore even more excellent forming properties can be obtained.

The shape of the fine particles (primary particles) of the calcium hydrogen phosphate is not particularly limited herein, and they can be squamous, columnar, or spherical, etc., but squamous particles are particularly preferred. More specifically, the desired squamous particles can be obtained by limiting the above crystallite size to no more than 300 Å.

The fine particles of calcium hydrogen phosphate of the present invention have excellent forming properties. For example, when the fine particles are formed into a tablet (pellet-shaped compressed powder), an even greater hardness than with prior art fine particles can be obtained with the same compressive force. More specifically, the hardness of tablets (average value of 10 tablets) obtained by forming a sample prepared by mixing the fine particles of the present invention with magnesium stearate (average particle size 6 μm) at a weight ratio of 99.5:0.5 with an eccentric type tablet press (punch diameter of 9 mm, tablet weight of 300 mg, and compression of 1.0 ton) is normally at least 40 N, preferably at least 100 N, and more preferably at least 120 N.

In addition, if the amount of acid sites of the fine particles of calcium hydrogen phosphate of the present invention originates from the surface of the calcium hydrogen phosphate itself, preferably it will lie in the general range of about 0.3 to 0.5 $nm^{-2}$, but if the acid center originates from impurities, etc., the amount of acid sites can lie outside that range.

The above fine particles of calcium hydrogen phosphate can be more suitably obtained by the preparation method described below. This is a method for preparing the fine particles of calcium hydrogen phosphate with the formula $CaHPO_4 \cdot nH_2O$ (wherein n represents $0 \leq n \leq 0.5$) from tribasic calcium phosphate (calcium tertiary phosphate), the method comprising:

(1) a step of adding to a mixture containing tribasic calcium phosphate and a solvent (addition step); and (2) a step of heating the mixture (heat treatment step).

Addition Step

In the addition step phosphoric acid is added to a mixture containing tribasic calcium phosphate and a solvent. One of the most important features of this method is the use of tribasic calcium phosphate as the starting material. By using this raw material it is possible to suitably produce fine particles of calcium hydrogen phosphate that exhibit excellent handling properties, mixing properties, etc., while maintaining excellent forming properties:

Tribasic calcium phosphate is a compound with the chemical formula $Ca_3(PO_4)_2$, and a commercially available product can be used therefor. Tribasic calcium phosphate prepared by a publicly known manufacturing method can also be used. For example, tribasic calcium phosphate obtained by reacting a calcium-containing compound with a phosphoric acid compound in liquid phase can be used. More specifically, tribasic calcium phosphate can be used that is obtained by reacting at least one type of calcium-containing compound selected from a group consisting of calcium oxide, calcium hydroxide, calcium carbonate, calcium hydrogen carbonate, calcium chloride, calcium sulfate, calcium nitrate, and calcium alkoxide with phosphoric acid in water.

First a mixture of tribasic calcium phosphate and solvent is prepared. Any solvent that does not react with tribasic calcium phosphate can be used, and other than water, an alcohol, etc., can also be used. The use of water as a solvent is particularly preferred in the present invention. A slurry or water content-adjusted mixture containing tribasic calcium phosphate obtained by reacting the calcium-containing compound and phosphoric acid compound in a liquid medium can also be used as the above mixture. More specifically, as the above mixture a slurry of tribasic calcium phosphate obtained by reacting calcium hydroxide and phosphoric acid in water can be used either unchanged or after the water content thereof has been adjusted. The solid content of tribasic calcium phosphate in the mixture is not particularly limited herein, and normally it can be suitably adjusted to a range of about 10 to 50 wt % of the mixture.

Next phosphoric acid ($H_3PO_4$) is added to the mixture. The phosphoric acid ($H_3PO_4$) can be added as is, or it can be added in the form of an aqueous solution.

In general, the temperature when adding the phosphoric acid can be suitably adjusted within a range of no more than 50° C.

In the addition step it is preferable to add at least one type of acid (other than phosphoric acid) and a salt thereof (i.e., a habit modifier). By adding a habit modifier it is possible to limit the crystallite size, particle shape, etc., of the resulting fine particles. More specifically, it is possible to obtain particles with an even smaller crystallite size more reliably, and obtain even better forming properties thereby.

As noted above, at least one type of acid (other than phosphoric acid) and a salt thereof can be suitably selected and used as a habit modifier. Examples of the acid include inorganic acids such as pyrophosphoric acid, condensed phosphoric acids (for example, tri-polyphosphoric acid), tetrapolyphosphoric acid, and hexapolyphosphate); and polyhydric organic acids such as citric acid, tartaric acid, ethylenediamine tetraacetate (EDTA), malic acid, and succinic acid. An alkali metal salt, alkaline earth metal salt, etc., of these acids can be used as the above salt. In the present invention using 1) a polyhydric organic acid and salt thereof, and 2) at least one type of pyrophosphoric acid or condensed phosphoric acid and the salts thereof is particularly preferred. For example, using at least one of citric acid and at least on pyrophosphoric acid, and the salts thereof is more preferred.

The timing of adding the habit modifier is not particularly limited herein, and can be either before, during, or after the addition of the phosphoric acid. In particular, adding the habit modifier before adding the phosphoric acid is desirable from the standpoint of restricting the crystallite size of the resulting fine particles to no more than 300 Å.

It is preferable to set the amount of habit modifier to be added within the range of 1 to 40 mol % as a ratio of the tribasic calcium phosphate to the calcium. Adding habit modifier within this range enables the effects of the addition to be obtained even more effectively.

The habit modifier can be added as is or as a solution. When the habit modifier is used as a solution, preparing an aqueous solution thereof is particularly preferred.

Heat Treatment Step

In the heat treatment step, a heat treatment is performed on the mixture to which the above phosphoric acid has been added. In the heat treatment step calcium hydrogen phosphate is generated by the reaction of tribasic calcium phosphate and phosphoric acid.

The temperature of the heat treatment is not particularly limited herein provided the above reaction proceeds, but normally setting the temperature higher than 50° C., particularly within the range of 55° C. to 95° C., is preferred, and within the range of 60° to 95° C. is even more preferred.

The product resulting from the heat treatment step is normally in the form of a slurry, and the solids can be recovered as needed by filtration, centrifugation, or another publicly known solid-liquid separation method. In such a case, the mixture can be rinsed with water before and after the solid-liquid separation as needed. The resulting solids can be dried as needed. After drying, the solids can be additionally processed by pulverizing, classification, etc., as needed.

Furthermore, in the present invention the particle size can be adjusted as needed by additionally pulverizing the above slurry (wet pulverization; before the above solid-liquid separation procedure.

The fine particles of calcium hydrogen phosphate obtained in the above manner can be suitably used as the raw material powder in the present invention. These calcium hydrogen phosphate fine particles can also be granulated by a granulation method noted above.

EXAMPLES

The features of the present invention are described in even greater detail below through examples. However, the scope of the present invention is by no means limited thereto.

Example 1

Figure 1:
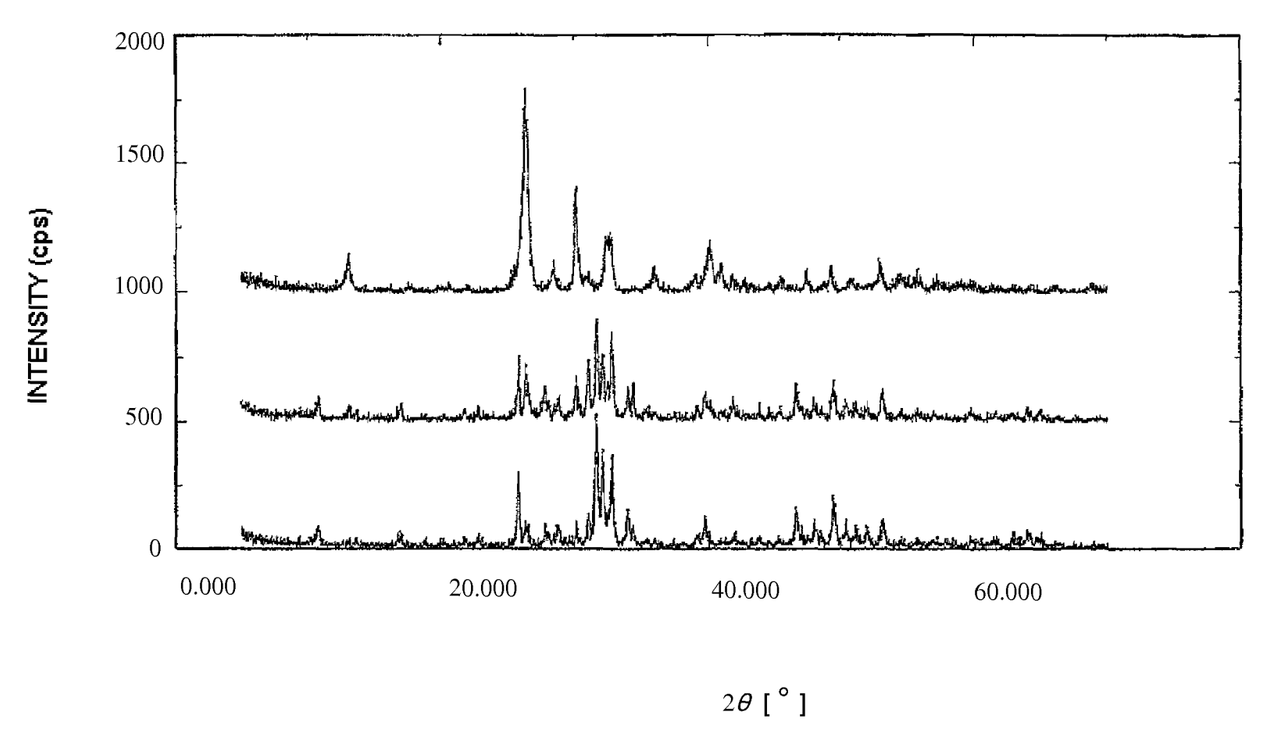
FIG. 1 is a graph showing the results of x-ray diffraction analysis of the calcium hydrogen phosphate obtained in Example 1.

First 191 g of calcium hydroxide was suspended in water and heated to 80° C. Then 193 g of 85% aqueous phosphoric acid was dropped thereinto, and the temperature was held at 80° C. for 30 min. After the reaction was completed a slurry of tribasic calcium phosphate (Slurry A) was obtained. After Slurry A was cooled to not more than 50° C., 13.7 g of anhydrous citric acid was added thereto, 91 g of 85% aqueous phosphoric acid was added, and the mixture was heated to 90° C. After the temperature had been held at 90° C. for 1 h, the reaction was completed. A powder was obtained by filtering and rinsing the reaction product with water, and drying the filtrate in a shelf-type dryer. The resulting powder was analyzed by powder x-ray crystallography, and the results are shown in FIG. 1. FIG. 1 shows three plots—the lower line is the starting material (Slurry A), the middle line is after the addition of phosphoric acid, and the upper line is the reaction product (the above powder). As one can clearly see from these results, it was confirmed that the above powder was calcium hydrogen phosphate.

The data for the plots in FIG. 1 (measurement conditions, etc.) are shown below.

Example 1

After Phosphoric Acid Addition, Starting Material

| | |
|---|---|
| Sample name: | Starting material |
| File: | .0158 |
| Comment: | Tribasic calcium phosphate |
| Measurement date: | 08 Aug. 2007 15:28 |
| Analyst | RINT |
| X-rays | Cu K-ALPHA1/40 kV/20 mA |
| Goniometer: | RINT2000 vertical goniometer |
| Attachment: | Reference sample holder |
| Filter: | Not used |
| Incident monochrome: | |
| Counter monochromator: | Fully automatic monochromator |
| Divergence slit: | ½ deg |
| Scattering slit: | ½ deg |
| Receiving slit: | 0.15 mm |
| Counter: | Scintillation counter |
| Scanning mode: | Continuous |
| Scanning speed: | 4.000°/min |
| Sampling width: | 0.020° |
| Scanning axis: | 2 θ/θ |
| Scanning range: | 5.000 to 70.000° |
| θ offset: | 0.000° |
| Fixed angle: | 0.000° |

The resulting calcium hydrogen phosphate was pulverized in a hammer pulverizer to obtain a powder having an average particle size of 12 µm, and that powder was then loaded into a high-speed mixer/granulator (model LFS-GS-2J manufactured by Fukae Powtech), water was added, and wet granulation was performed. After the granules had been dried for 24 hours at 80° C., they were sorted by sieve into 30 to 142 mesh products. The preparation conditions and properties of each sample are shown in Table 2.

Examples 2 to 5

The raw materials shown in Table 1 were loaded into a high-speed mixer/granulator (Fukae Powtech model LFS-GS-2J), water or a mixed solvent (ethanol:water=1:4 v/v) was added, and wet granulation was performed. After the granules had been dried for 24 h at 80° C., they were sorted by sieve into 30 to 142 mesh products. The preparation conditions and properties of each sample are shown in Table 2.

TABLE 1

| Example | Raw material |
|---|---|
| Ex. 2 | Same as in Example 1 |
| Ex. 3 | Silicon dioxide powder (Commercial product manufactured by Tomita Pharmaceutical Co. Ltd.: Silicon dioxide hydrate A1 pulverized with hammer pulverizer to average particle size of 20 µm) |
| Ex. 4 | Aluminum hydroxide (Commercial product manufactured by Tomita Pharmaceutical Co. Ltd.: Japanese Pharmacopoeia grade dry aluminum hydroxide gel, average particle size 6 µm |
| Ex. 5 | Aluminum silicate (Commercial product manufactured by Tomita Pharmaceutical Co. Ltd.: Japanese Pharmacopoeia grade synthetic aluminum silicate, average particle size 13 µm |

The solubility in water of each of the inorganic materials in Examples 1 to 5 was no greater than 1 g/30 mL at 20° C.

2. The measurement methods for each property are shown below.

(1) External Shape of Particles
Measured by scanning electron microscope.

(2) pH
The pH of a liquid prepared by suspending 2.0 g of the test sample in 50 mL of water (25° C.) was measured using a pH meter.

(3) Particle Hardness
A particle hardness tester (GRANO manufactured by Okada Seiko Co., Ltd.) was used to measure the peak value (g) of crush strength of a single particle, and the average value of 20 particles was determined thereby.

(4) Angle of Repose
A hopper was positioned 100 mm above a 50 mm diameter plate, and a test sample was dropped from the hopper in small increments to form a conical pile of test sample. The angle of repose was calculated from the height (h) of the pile of test sample when it had stabilized without further sliding, the angle formed by the plate, and the slope of the pile (angle of repose $\alpha = \tan^{-1}$ (h/25 mm).

(5) Bulk Density
First 20 g of test sample was placed in a 50 mL graduated cylinder. Then the cylinder was placed in a tapping machine (model TMP-7-P manufactured by Tsutsui Scientific Instruments, Co., Ltd.), and after testing was performed at a tap number of 100, tapping height of 4 cm, and tapping speed of 36 times/min, the volume F (mL) was measured by visual observation. Then the bulk density (g/mL) was calculated by 20/F.

TABLE 2

| | Item | Example 1 | Example 2 | Example 3 | Example 4 | Example 5 |
|---|---|---|---|---|---|---|
| Raw material | Ingredient | Calcium hydrogen phosphate | Calcium hydrogen phosphate | Silicon dioxide hydrate | Aluminum hydroxide gel | Synthetic aluminum silicate |
| | Granulator load | 200 g | 200 g | 200 g | 300 g | 300 g |
| Granulation conditions | Solvent | Water | Water:ethanol = 8:2 (v/v) | Water | Water | Water |
| | Amount solvent added | 80 mL | 95 mL | 440 mL | 240 mL | 120 mL |
| | Agitator speed | 720 rpm | 720 rpm | 720 rpm | 720 rpm | 720 rpm |
| | Chopper speed | 1200 rpm | 1200 rpm | 1200 rpm | 1200 rpm | 1200 rpm |
| Properties | Shape | Spherical | Spherical | Spherical | Spherical | Spherical |
| | pH (4% suspension) | 6.9 | 6.9 | 5.9 | 7.8 | 7.7 |
| | Particle hardness | 260 g/mm$^2$ | 570 g/mm$^2$ | 380 g/mm$^2$ | 270 g/mm$^2$ | 220 g/mm$^2$ |
| | Angle of repose | 26.2° | 26.2° | 30.1° | 31.2° | 32.4° |
| | Bulk density | 1.000 g/mL | 0.95 g/mL | 0.33 g/mL | 0.36 g/mL | 0.56 g/mL |
| | Size distribution | | | | | |
| | ≥500 µm | 0.5% | 0.4% | 0.2% | 0.1% | 0.2% |
| | 45 to 500 µm | 99.0% | 99.3% | 99.5% | 99.3% | 98.9% |
| | ≤45 µm | 0.5% | 0.3% | 0.3% | 0.6% | 0.9% |

Test Example 1

The external shape, pH (pH in liquid of 4% suspension), particle hardness, angle of repose, bulk density, and particle size distribution were measured for the core particles obtained in each example, and the results are shown in Table (6) Particle Size Distribution
After a test sample was sonicated (frequency 400 Hz), it was dispersed in water and the particle size distribution in aqueous medium was measured by laser refractometry. A MICROTRAC HRA Model No. 9320-X100 manufactured by Honeywell was used for the measurement.

Test Example 2

The amount of acid sites of the calcium hydrogen phosphate obtained in Example 1 was tested, and the results are shown in Table 3.

TABLE 3

| Sample | Per weight/mol kg$^{-1}$ | | | | Per surface area/nm$^{-2}$ | | | |
|---|---|---|---|---|---|---|---|---|
| | [Na] | [Al] | [S] | Amount of acid sites | [Na] | [Al] | [S] | Amount of acid sites |
| Ex. 1 | $6.3 \times 10^{-3}$ | $3.7 \times 10^{-3}$ | $7.7 \times 10^{-3}$ | 0.020 | 0.13 | 0.08 | 0.16 | 0.41 |

Amount of acid sites was measured by the following procedure. A sample of about 0.1 g was set in the quartz cell (internal diameter: 10 mm) of a temperature programmed desorption apparatus (TPD-AT-1 manufactured by BEL Japan, Inc.), and the temperature was raised to 673 K (400° C.) at 10 K·min$^{-1}$ under a stream of oxygen gas ($O_2$) (60 cm$^3$·min$^{-1}$, 1 atm) and then held at 673 K for 1 hour. Subsequently, with the $O_2$ stream maintained, the temperature was lowered to 373 K (100° C.), the system was subjected to vacuum degassing, 100 Torr (1 Torr=1/760 atm=133 Pa) of $NH_3$ was introduced and allowed to undergo adsorption for 30 minutes, and the system was then evacuated for 30 minutes and subsequently subjected to a steam treatment. In the steam treatment, steam having a steam pressure of approximately 25 Torr (approximately 3 kPa) was introduced at 100° C., the system was held in that state for 30 minutes, the system was evacuated for 30 minutes, steam was re-introduced for an additional 30 minutes, and then an evacuation was repeated again for 30 minutes. Subsequently, helium gas was supplied to the system at a rate of 0.041 mmol·s$^{-1}$ (equivalent to 60 cm$^3$·min$^{-1}$ at 298 K, 25° C. and 1 atm) while a state of reduced pressure (100 Torr) was maintained, and after maintaining this state for 30 minutes at 100° C., the sample bed was heated to 1073 K (800° C.) at 10 K·min$^{-3}$, and the evacuated gas was analyzed using a mass spectrometer (ANELVA M-QA 100F) (Katada and Niwa, Zeolite, 21, 45 (2004); N. Katada and M. Niwa, Catal. Surveys Asia, 8, 161 (2004)). During measurement, mass spectra were recorded for mass value (m/e) of 2, 4, 14, 15, 16, 17, 18, 26, 27, 28, 29, 30, 31, 32 and 44. Following completion of the measurements, a 1 mol % $NH_3$/He standard gas was further diluted with helium, and gas samples having $NH_3$ concentrations of 0, 0.1, 0.2, 0.3 and 0.4 mol % were passed through the detector with the total flow rate set to 0.041 mmol·s$^{-1}$, spectra were recorded, and an ammonia gas calibration curved was prepared and used to correct the detector strength. The analysis of ammonia absorption followed the published principles (N. Kazada, H. Igi, J.- H. Kim and M. Niwa, J. Phys. Chem., B, 101, 5969 (1997).

Example 6

After the core particles obtained in Example 2 were sorted, a film (coating) containing an active ingredient was formed on the surface thereof.

<Sorting Procedure>

First, the core particles obtained in Example 2 were further sorted into categories of 45 to 350 μm, 45 to 150 μm, and 350 to 500 μm. The external shape, pH (pH in liquid of 4% suspension), particle hardness, angle of repose, bulk density, and particle size distribution were measured for each sorted product in the same manner as in Test Example 1, and the results are shown in Table 4.

TABLE 4

| | Example 2-A (45-350 μm) | Example 2-B (45-150 μm) | Example 2-C (350-500 μm) |
|---|---|---|---|
| Shape | Spherical | Spherical | Spherical |
| pH (4% suspension) | 6.9 | 6.9 | 6.9 |
| Particle hardness | 430 g/mm$^2$ | 300 g/mm$^2$ | 320 g/mm$^2$ |
| Angle of repose | 26.0° | 25.2° | 27.2° |
| Bulk density | 0.98 g/mL | 0.98 g/mL | 0.92 g/mL |
| Size distribution | | | |
| ≥500 μm | 0.0% | 0.0% | 0.2% |
| 350-500 μm | 0.1% | 0.0% | 99.3% |
| 150-350 μm | 33.2% | 0.5% | 0.0% |
| 45-150 μm | 65.9% | 98.6% | 0.1% |
| ≤45 μm | 0.8% | 0.9% | 0.1% |

<Coating Procedure>

Next, in addition to the samples shown in Table 4 (Example 2-A, Example 2-B, and Example 2-C), commercially available organic core particles were coated with the recipes shown in Table 5. More specifically, 210 g of the core particles and 45 g of acetaminophen were loaded into a rotary fluidized bed dryer (Multiplex MP-01, manufactured by Powrex Corporation) and fluidized at a rotating disk speed of 50 rpm, air flow of 45 m$^3$/hr, and set temperature of 60° C. Then 280 g of coating liquid was sprayed thereinto for 60 min. After coating, the particles were fluidized and dried for 10 min at an air flow of 45 m$^3$/hr and set temperature of 60° C., the particles were fluidized and cooled for 10 min at an air flow of 45 m$^3$/hr, and set temperature of 30° C. to obtain spherical particles coated with acetaminophen.

TABLE 5

| | | Recipe A | Recipe B | Recipe C | Recipe D |
|---|---|---|---|---|---|
| Core particles | Example 2-A | 210 g | — | — | — |
| | Example 2-B | — | 210 g | — | — |
| | Example 2-C | — | — | 210 g | — |
| | Commercial organic particles | — | — | — | 210 g |
| Drug | Acetaminophen | 45 g | 45 g | 45 g | 45 g |
| Binder | Coating liquid | 280 g | 280 g | 280 g | 280 g |

The following items were used for the "commercial organic particles," "acetaminophen," and "coating liquid" in Table 5.

Commercial organic particles: "Nonpariel-105" (manufactured by Freund Corporation, components: lactose and crystalline cellulose)

Acetaminophen: Acetaminophen (manufactured by Yamamoto Corporation)

Coating liquid: Liquid prepared by adding water to 7 g of hydroxypropyl methylcellulose (HPMC: Shin-Etsu Chemical Co., Ltd.) and bringing the total volume to 280 g <Properties of Acetaminophen-Coated Spherical Particles>

The following tests were performed on the acetaminophen-coated spherical particles (samples A to D) obtained by the above coating procedure.

(1) Dissolution Test

Dissolution tests under the conditions noted below were performed on the resulting acetaminophen-coated spherical particles in accordance with the test method for acetaminophen tablets in the Japanese Pharmaceutical Codex, part 3.

For the analytical device a dissolution test station (model SR8Plus-8S manufactured by Hanson Research Corporation) was used.

The test conditions were as follows: test liquid: 900 mL water, paddle speed: 50 rpm, test weight: 1.5 g (200 mg as acetaminophen), sampling times: 5, 10, 15, 20 and 30 min.

For the analytical method the absorbance at a wavelength of 244 nm was measured by UV-visible absorbance (spectrophotometer, model U-3210, manufactured by Hitachi, Ltd.), and the amount of acetaminophen in each sampling liquid was analyzed. The dissolution rate was calculated by assigning a dissolution rate of 100% to corresponding weight of 200 mg acetaminophen. The results are shown in Table 6.

TABLE 6

| Sampling time | Dissolution Rate | | | |
|---|---|---|---|---|
| | Coated spherical particles of recipe A (sample A) | Coated spherical particles of recipe B (sample B) | Coated spherical particles of recipe C (sample C) | Coated spherical particles of recipe D (sample D) |
| 5 min | 91.2% | 92.3% | 91.1% | 91.0% |
| 10 min | 97.4% | 98.0% | 96.8% | 96.4% |
| 15 min | 99.3% | 99.3% | 98.4% | 98.4% |
| 20 min | 99.6% | 99.7% | 98.8% | 99.0% |
| 30 min | 99.9% | 99.9% | 99.8% | 99.9% |

(2) Stability Test

A portion of the acetaminophen-coated spherical particles from each sample was placed in an aluminum laminate bag of polyethylene/aluminum/polypropylene and sealed. The bags were stored under refrigeration and used as reference samples. The remaining particles were placed in a constant temperature, constant moisture chamber under conditions of 40° C. and 75 RT %, let stand for 3, 15, and 30 days, and used as samples for evaluation.

The color of the reference samples and samples for evaluation was measured using a colorimeter (model Z-300A manufactured by Nippon Denshoku Industries Co., Ltd.), and the difference in color between the color of the evaluation sample (E1) and the color of the reference sample (E0) was determined (color difference ΔE: E1-E0). The results are shown in Table 7.

TABLE 7

| Elapsed time | Color difference ΔE | | | |
|---|---|---|---|---|
| | Coated spherical particles of recipe A (sample A) | Coated spherical particles of recipe B (sample B) | Coated spherical particles of recipe C (sample C) | Coated spherical particles of recipe D (sample D) |
| 3 days | 0.76 | 0.80 | 1.10 | 1.10 |
| 15 days | 1.03 | 0.90 | 1.33 | 1.27 |
| 30 days | 1.36 | 1.20 | 1.68 | 1.57 |

It is clear from the results in Table 7 that samples A to C formed using core particles of the present invention can exhibit both solubility and stability performance equal to or better than core particles formed using the commercially available organic compound (sample D). In particular, the color difference ΔE in sample A and sample B formed from particles of relatively small size is no more than 1.50 (particularly, no more than 1.40), and these samples can exhibit greater stability than organic core particles.

Thus, the core particle of the present invention not only solves the problems associated with organic core particles, but excellent core particle performance that is equal to or better than organic core particles can be obtained thereby.

The invention claimed is:

1. A core particle for pharmaceutical preparation of a drug-containing particle comprising the core particle and a film containing a pharmaceutical ingredient formed on the surface of the core particle, wherein
  (1) the core particle comprises a pharmaceutically acceptable inorganic material,
  (2) the inorganic material is poorly soluble in water,
  (3) the pH of the inorganic material is 5 to 8,
  (4) the core particle is obtained by wet granulation of a composition containing the inorganic material, the granulation method being stirred granulation method,
  (5) the core particle does not contain an active pharmaceutical ingredient,
  (6) the core particle is spherical,
  (7) the core particle has an average particle size of 150 μm or more, and
  (8) the particle hardness of the core particle is at least 200 g/mm2,
  wherein the inorganic material contains fine particles of calcium hydrogen phosphate represented by the formula $CaHPO_4 \cdot nH_2O$ wherein n represents $0 \leq n \leq 0.5$, and wherein
  (1) an average secondary particle size of the fine particles is no more than 15 μm, and
  (2) a static apparent specific volume of the fine particles is less than 5 mL/g.

2. The core particle for pharmaceutical preparation according to claim 1, having a particle size distribution of no more than 5 wt % of a particle with a diameter less than 350 μm, at least 90 wt % of a particle with a diameter at least 350 μm but less than 500 μm, and no more than 5 wt % of a particle with a diameter at least 500 μm.

3. The core particle for pharmaceutical preparation according to claim 1, wherein the core particle is formulated so that at least 90 wt % thereof is a pharmaceutically acceptable inorganic material.

4. The core particle for pharmaceutical preparation according to claim 1, wherein the inorganic material has a solubility in water of no more than 1 g/30 mL at 20° C.

5. The core particle for pharmaceutical preparation according to claim 1, wherein the inorganic material further comprises at least one substance selected from silicon dioxide, aluminum hydroxide, and aluminum silicate.

6. The core particle for pharmaceutical preparation according to claim 1, wherein the pH of the fine particles lies within a range of 6 to 8.

7. The core particle for pharmaceutical preparation according to claim 1, wherein a crystallite size of the fine particles is no more than 300 Å.

8. The core particle for pharmaceutical preparation according to claim 1, wherein the static apparent specific volume of the fine particles is no more than 4.8 mL/g.

9. A drug-containing particle, obtained by forming a film containing a pharmaceutical ingredient on the surface of the core particle for pharmaceutical preparation according to claim 1.

10. The drug-containing particle according to claim 9, wherein the film contains a pharmaceutical ingredient and excipient.

11. A process for producing a drug-containing particle, the process comprising a step of forming a film containing a pharmaceutical ingredient on the surface of the core particle for pharmaceutical preparation according to claim 1.

12. The core particle for pharmaceutical preparation according to claim 1, wherein the average particle size is 350 μm or more.

* * * * *